United States Patent
Brusilow

Patent Number: 6,130,035
Date of Patent: Oct. 10, 2000

[54] USE OF OROTIDINE MONOPHOSPHATE DECARBOXYLASE INHIBITION IN A METHOD FOR CANCER SCREENING

[75] Inventor: Saul W. Brusilow, Baltimore, Md.

[73] Assignee: Brusilow Enterprise LLC, Baltimore, Md.

[21] Appl. No.: 09/240,866

[22] Filed: Feb. 1, 1999

Related U.S. Application Data

[60] Provisional application No. 60/075,620, Feb. 20, 1998.

[51] Int. Cl.[7] .............................. C12Q 1/00; G01N 33/48
[52] U.S. Cl. .................................. 435/4; 436/63; 436/64
[58] Field of Search .................................. 435/4; 436/63, 436/64

[56] References Cited

PUBLICATIONS

Beardmore et al.; J. Lab Clin. Med. 78:696–704, 1971.
Bono et al.; J. Clin. Invest. 43:1486–1494, 1964.
Cardoso et al.; Cancer Res. 21:1551–1556, 1961.
Christopherson et al.; Eur. J. Biochem. 134:331–335, 1983.
Fallon et al.; J. Clin. Invest. 40:1906–1914, 1961.
Fallon et al.; Amer. J. Med. 33:526–537, 1962.
Goldenthal, E.J.; Toxicology and Applied Pharmacology 18:185–207, 1971.
Handschumacher R.E.; J. Biol. Chem. 235:2917–2919, 1960.
Krenitsky et al.; J. Biol. Chem. 242:2675–2682, 1967.
Krooth et al.; Cell 3:55–57, 1974.
Levine et al.; Biochemistry 19:4993–4999, 1980.
Pasternak et al.; J. Biolg. Chem. 234:2992–2997, 1959.
Pinsky et al. Proc. Nat'l. Acad. Sci. 57:1267–1274, 1967.
Potvin et al.; Biochem. Pharm. 27:655–665, 1978.
Sans et al.; Pharmazie 43:827–829, 1988.
Simmonds et al.; Clinical Science 80:191–197, 1991.
Traut et al.; Biochem Pharm. 26:2291–2296, 1977.
Traut et al.; Progress in Nucleic Acid Research and Molecular Biology 53:1–78, 1996.
Welch et al.; Cancer Chemotherapy Reports 9:39–46, 1960.
Carducci et al.; In vivo 12:271–274, 1998.
Hauser et al.; New England J. of Med.; 322:1641–1645, 1990.

*Primary Examiner*—Yvonne Eyler
*Assistant Examiner*—Anne L. Holleran
*Attorney, Agent, or Firm*—Arent Fox Kintner Plotkin Kahn

[57] ABSTRACT

The present invention provides a method of screening for the presence or absence of cancer characterized by increased DNA synthesis. The present invention also provides a method of monitoring the effectiveness of treatment of cancer characterized by increased DNA synthesis. The methods are based on the observation that increased de novo pyrimidine biosynthesis is characteristic of malignant solid tumors. An initial step of pyrimidine biosynthesis is the conversion of orotidine monophosphate (OMP) to uridine monophosphate by OMP decarboxylase which is inhibited by mononucleotide precursors such as 6-hydroxyuridine, 6-azauridine, uridine, allopurinol and oxipurinol. Inhibition of OMP decarboxylase results in accumulation of orotidine and orotate which can be measured in a urine sample. The accumulation of oritidine and orotate, in amounts above that of a control, provides an indicator that the subject has a cancer characterized by having increased DNA synthesis.

11 Claims, 1 Drawing Sheet

USE OF OROTIDINE MONOPHOSPHATE DECARBOXYLASE INHIBITION IN A METHOD FOR CANCER SCREENING

This application claims priority under 35 U.S.C. 119(e) to provisional application No. 60/075,620, filed Feb. 20, 1998.

BACKGROUND OF THE INVENTION

The pathway of uridine monophosphate synthesis has been studied extensively and is reasonably well understood. It has been determined that oritidine monophosphate (OMP) decarboxylase catalyzes the conversion of oritidine monophosphate to uridine monophosphate, in the de novo biosynthesis of pyrimidines, an initial step in de novo DNA synthesis. It has also been determined that OMP decarboxylase is inhibited by a range of mononucleotides, the precursors of which include barbiturate (a.k.a. 6-hydroxyuridine), 6-azauridine, uridine, allopurinol and oxipurinol. Levine et al, *Biochem.* 19:4993–4999 (1980); Potvin et al, *Biochem. Pharm.* 27:655–665 (1978); Hauser et al, *N. Engl. J. Med.* 322:1641–1645 (1990). The inhibition of OMP decarboxylase results in the accumulation of orotidine and orotate. The pathway of pyrimidine mononucleotide biosynthesis and the mechanism of action of various OMP decarboxylase inhibitors and precursors thereof is shown in FIG. 1.

Allopurinol induced pyrimidinuria (orotic aciduria and/or orotidinuria) has been shown to be a sensitive and specific test that identifies the increased de novo pyrimidine mononucleotide biosynthesis accompanying ornithine transcarbamylase (OTC) deficiency. The test has been standardized and helps to establish a diagnosis in women at risk for having a mutation at the OTC locus on the X chromosome. Hauser et al, *N. Engl. J. Med.* 322:1641–1645 (1990), correction *N. Engl. J Med.* 336:1335 (1997); Burlina et al, *J. Inher. Metab. Dis.* 15:707–712 (1992); Pineda et al, *Medicina Clinica* 101:383–386 (1993); Maestri et al, *Amer. J. Hum. Genet.* 59:A378 (1996). In this prior test, allopurinol is administered to patients, and the levels of orotate and/or orotidine were measured. Orotate and oritidine levels are considered abnormal if they are three standard deviations above the mean value of normal (control) samples.

It is desirable to have a screening process which detects cancer in its early stages. Such a screening process may be an invaluable tool in detecting the cancer in time for early treatment, which translates into a higher survival rate and less traumatic recovery for the patient. A screening process that is non-invasive is highly desirable, to ensure that patients will be willing to undergo the screening process. A screening process is most useful when it can follow the history of a patient who is at risk of developing cancer, due to genetic history or other statistical measure of risk.

The present inventor has discovered that increased de novo pyrimidine biosynthesis (and, hence, de novo DNA biosynthesis), which is a characteristic of malignant solid tumors, may be determined by using OMP decarboxylase inhibitor precursors. This discovery may be incorportated into a screening process for determining the presence or absence of cancer. This discovery can also be used to monitor the effectiveness of cancer treatment.

SUMMARY OF THE INVENTION

Thus, the present invention is directed to a method of screening for the presence or absence of cancer characterized by increased DNA synthesis in a patient, the method comprising administering to the patient an orotidine monophosphate decarboxylase inhibitor precursor;

thereafter collecting a body fluid sample from the patient; and determining the content of orotate or orotidine in the sample relative to a standard or control to correlate the content with the presence or absence of cancer in the patient.

The present invention is also directed to a method of monitoring the effectiveness of treatment of cancer characterized by increased DNA synthesis in a patient, the method comprising (a) administering to the patient an orotidine monophosphate decarboxylase inhibitor precursor;

(b) thereafter collecting a body fluid sample from the patient;

(c) determining a first orotate or orotidine content in the sample;

(d) thereafter treating the cancer with a cancer treatment;

(e) repeating steps (a)–(c) to determine a second orotate or orotate content in the sample; and (f) comparing the first content with the second content to monitor the effectiveness of the cancer treatment.

DESCRIPTION OF THE PREFERRED EMBODIMENTS

Figure 1:
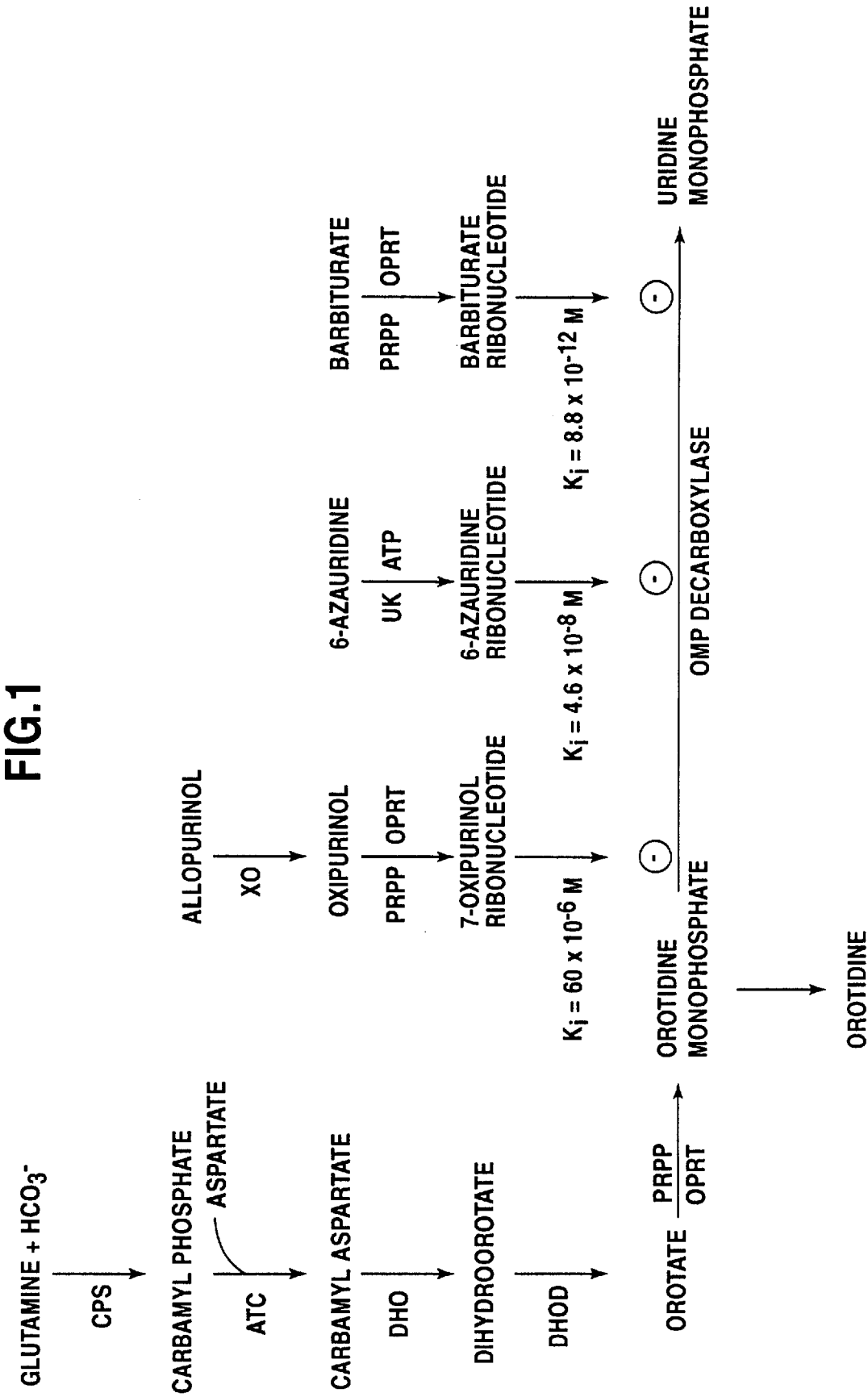
FIG. 1 shows the pathway of uridine monophosphate biosynthesis and its inhibition at the orotidine monophosphate decarboxylase step by a variety of inhibitors.

In the present methods, the body fluid sample is preferably a urine sample. Collection of a urine sample is the least invasive form of collection. However, other body fluid samples such as blood or serum may also be used.

The OMP decarboxylase inhibitor precursor is preferably selected from the group consisting of 6-hydroxyuridine, 6-azauridine, uridine, allopurinol and oxipurinol. Due to its high $K_i$ value, 6-hydroxyuridine is most preferred. It is understood that any of the OMP decarboxylase inhibitor precursors may be used in these methods, as the selection of a particular inhibitor precursor is not critical to the invention.

In a preferred embodiment, the OMP decarboxylase inhibitor precursor is administered to the patient at a dose of about 0.1 to 15 mg/kg per day, more preferably 0.5 to 10 mg/kg per day. Of course, dosage selection and modification of these values is well within the skill of an ordinary worker in the art, depending on the particular need of the patient involved.

The collecting step preferably occurs in a period of about 1–30, more preferably about 1–10 hours after the OMP decarboxylase inhibitor precursor is administered. In one embodiment, several samples are collected over sequential periods after the administration of the OMP decarboxylase inhibitor precursor, starting about 1–10 hours after the administration of the OMP decarboxylase inhibitor precursor, preferably about 6 hours. Preferably, the collecting step is repeated at least once. More preferably, the collecting step is repeated 2–4 times. The content of orotate or orotidine in each collecting step is averaged, and the average content is thereafter used in the determining step which follows. Each collecting step occurs sequentially in a period of about every 2–10 hours after the first collecting step, more preferably about every 6 hours. In an alternative embodiment, an 18–24-hour urine sample collection is conducted. Urine is collected for a period of 18–24 hours after administration of the OMP decarboxylase inhibitor precursor, and the content of orotate or orotidine is determined from the total urine collected, rather than in individual urine fractions.

In the screening method according to the invention, the determining step compares the orotate or orotidine content in the sample relative to a standard or control. From this comparison, it may then be determined whether the patient is positive or negative for the presence of cancer. The comparison may be an amount-to-amount comparison between the sample and the standard or control, or the comparison may be a relative determination (i.e., determining whether there is more or less orotate or orotidine in the sample than in the standard or control, but not determining the exact amount of orotate or orotidine in the sample). The standard or control may reflect a threshold value indicative of the presence of cancer, or the standard or control may reflect "normal" (i.e., non-cancer) values. Relative determinations may be made, for example, using gel assays, immunoassays, bacterial growth assays, gas chromatography, mass spectroscopy or standard curves.

All types of cancer may be screened for using the method of the invention, as long as the cancer is characterized by the increase in DNA synthesis. It is preferred that the increase in DNA synthesis is statistically significant. Since only DNA synthesis is being determined, and a diagnosis of a particular cancer type is not being made using the present test, there is no limit to the type of cancer to which the present invention is applicable. Once a patient is determined to be positive in the present screening test, other diagnostic tests would be employed to determine the type of cancer afflicting the patient.

In the method of the invention to monitor the effectiveness of cancer treatment, a first orotate or orotidine content in the sample is determined before a particular cancer treatment is undergone. Thereafter, the cancer is treated with a cancer treatment specific for the type of cancer afflicting the patient. The type of cancer treatment is not a part of the present invention, therefore, no additional details on the specific cancer treatment are deemed necessary. Thereafter, a second orotate or orotidine content in the sample is determined, and the first content is compared with the second content. If the content of the orotate or orotidine diminishes in the second sample, the cancer treatment is considered effective.

However, if the orotate or orotidine content does not diminish, the cancer treatment is considered ineffective. Thus, the present invention is a useful monitor for the effectiveness of cancer treatment.

A kit for use with the methods of the invention is also a subject matter of the present application. The kit comprises an OMP decarboxylase inhibitor precursor, along with at least one additional component. The additional component may be, for example, a standard or control, a standard curve or other information allowing a worker of skill in the art to determine the presence or absence of cancer in a patient by comparing the patient's sample with the information, or an apparatus or composition of matter (such as an antibody or bacterial growth assay) for determining the orotate or orotidine content in the sample.

EXAMPLE: Administration of Allopurinol for Cancer Screening

Eleven patients (8 males, 3 females) with proven solid tumor malignancy took part in the test. Ten patients completed the allopurinol test; an additional patient had elevated orotidinuria at baseline. A population-based control group of 30 subjects consisted of 21 normal women and 9 men, ranging in age from 30–70 years.

The allopurinol test protocol required five urine collection periods—a pre-allopurinol baseline collection (Period 0) at which time a 300 mg dose of allopurinol was taken, followed by four fractional urine collections (Periods 1,2,3,4), each separated by a 6 hour duration. Orotate, orotidine and creatinine were measured on aliquots of urine from each timed collection and results were expressed as the ratio of orotate or orotidine to creatinine.

The sensitivity and specificity of the allopurinol test to detect pyrimidinuria was established by assigning a positive result to any orotate or orotidine value four standard deviations or greater above the control mean value of the respective period. There was no statistical difference between control male and female subjects apart from the orotate values in period 3 which did not effect the sensitivity or specificity.

Table 1 summarizes the clinical status and diagnosis of the eleven patients. Patients had a wide variety of tumors; metastatic adenocarcinoma of the colon and hepatocellular carcinoma comprised 45% of the diagnoses. Seven of 11 had locally advanced, unresectable or metastatic disease.

TABLE 1

Patient Characteristics based on tumor node metastasis classification (TNM) by the American Joint Committee on Cancer (AJCC).

| Patient Number | Age | Sex | ECOG Performance Status | Diagnosis | Clinical Stage | Site of Metastasis | Survival |
|---|---|---|---|---|---|---|---|
| 1 | 28 | M | 1 | Hepatoma | III | Local | — |
| 2 | 38 | F | 1 | Hepatoma | III | Local | — |
| 3 | 69 | M | 2 | Colon Cancer | IV | Liver | + |
| 4 | 44 | M | 1 | Colon Cancer | IV | Liver | + |
| 5 | 73 | M | 1 | Colon Cancer | IV | Liver | + |
| 6 | 58 | F | 1 | Leiomyosarcoma | IV | Lung, bone abdomen | — |
| 7 | 60 | M | 1 | Renal Cancer | IV | Bone, lung | — |
| 8 | 59 | M | 1 | Carcinoid | IV | Liver | + |
| 9 | 40 | M | 1 | Squamous head/neck | II | Locally Recurrent | + |

TABLE 1-continued

Patient Characteristics based on tumor node metastasis classification (TNM) by the American Joint Committe on Cancer (AJCC).

| Patient Number | Age | Sex | ECOG Performance Status | Diagnosis | Clinical Stage | Site of Metastasis | Survival |
|---|---|---|---|---|---|---|---|
| 10 | 27 | M | 0 | Hodgkin/NS | IA | No | + |
| 11 | 79 | F | 1 | Gastric lymphoma | IIAE | No | + |

Abbreviations: ECOG, Eastern Cooperative Oncology Group

Table 2 shows the mean values and standard deviations of urine orotate and orotidine values in each of the five periods in a group of 30 control subjects compared to the results of the allopurinol test in 10 tumor patients and one tumor subject (patient #2), from whom only a baseline urine sample was obtained.

A positive test was defined as a urine orotate and/or orotidine level 4 standard deviations or greater above the control mean. At baseline 3 patients had a positive test; two of these patients and 5 others had a significant increase in the levels of urine orotate and/or orotidine after challenge with allopurinol. Thus, 8 of 11 patients had a positive test either prior to challenge with allopurinol or during one of the time periods. As expected, none of the control subjects had values greater than 4 standard deviations above the mean. All patients who completed the study and had a positive test had elevated levels in collection Period 4 (collected 18–24 hours after allopurinol administration).

standard deviations or greater above the mean control value of the respective period. That the pyrimidinuric response of many cancer patients is of greater magnitude than controls is suggested by the finding that 25 of the 27 samples which were 4 standard deviations above the mean were also 5 standard deviations above the mean; 59% of the values that were 4 standard deviations above the mean were also 10 standard deviations above the mean.

The magnitude of the pyrimidinuric response to allopurinol in this example suggests that the present test is sufficiently sensitive to detect early tumors. The test is thus useful in patients at high risk for cancer occurrence.

Abbreviations for FIG. 1.
  CPS, carbamyl phosphate synthetase II
  ATC, aspartate transcarbamyalse
  DHO, dihydroorotase
  DHOD, dihydroorotate dehydrogenase
  PRRP, phosphoribosylpyrophosphate

TABLE 2

Allopurinol test results in 30 control subjects (21 female, 9 male) compared to 11** patients with malignant tumors.
Underlined values are greater than 4 standard deviations above the mean value for the respective collection period.
Micromoles of Urine Orotate or Orotidine per Millimole of Creatinine

|  | Period 0 | | Period 1 | | Period 2 | | Period 3 | | Period 4 | |
|---|---|---|---|---|---|---|---|---|---|---|
|  | Orotate | Orotidine | Orotate | Orotidine | Orotate | Orotidine | Orotate | Orotidine | Orotate | Orotidine |
| Control Mean ± 1 SD* | 0.49 ± .29 | 0.49 ± .29 | 2.22 ± 1.22 | 0.66 ± .36 | 2.75 ± 1.73 | 1.93 ± 1.29 | 1.49 ± .88 | 2.02 ± .99 | .97 ± .66 | 2.02 ± 1.07 |
| 1 Hepatocellular Carcinoma | 28.7 | 1.26 | 114 | 17.5 | nt | nt | 390 | 89.6 | nt | nt |
| 2 Hepatocellualar Carcinoma** | 64.6 | 1.31 | nt | nt | | | | | | |
| 3 Colon Carcinoma | nd | 9.77 | 6.87 | 11.6 | 4.36 | 10.5 | 5.31 | 7.51 | 2.62 | 10.6 |
| 4 Colon Carcinoma | nd | nd | nd | nd | 2.72 | 3.99 | 4.62 | 12.5 | 4.68 | 12.7 |
| 5 Colon Carcinoma | nd | nd | nd | nd | 2.18 | 1.34 | 1.74 | 2.89 | 5.02 | 2.78 |
| 6 Lymphoma | 2.03 | nd | 14.7 | nd | 78.7 | 11.8 | 75.3 | 18.1 | 29.5 | 7.58 |
| 7 Leiomyosarcoma | nt | nt | 1.22 | 1.22 | 1.75 | 2.83 | 4.48 | 11.4 | nd | 7.61 |
| 8 Hodgkin's Disease | nd | nd | 1.28 | nd | 1.06 | 1.80 | 0.88 | 2.71 | 0.914 | 4.73 |
| 9 Squamous Cell Carcinoma | 0.84 | nd | nd | 3.15 | nd | 2.48 | nd | 1.03 | nd | 1.99 |
| 10 Renal Cell Carcinoma | nd | nd | nd | nd | 1.74 | 3.64 | nd | 3.77 | nd | 2.66 |
| 11 Carcinoid | nd | nd | nd | nd | nd | nd | nd | nd | 1.23 | nd |

*Neither orotate nor orotidine were detectable in many control subject collection periods (all baseline [Period 0] samples as well as 36 of the 240 other study periods). To account for these samples in performing statistical analysis, a value of 5 μmols per liter (the lowest reliably measureable concentration) of orotate or orotidine was assigned to such samples and the ratio calculated using the measured urine creatinine concentration of the respective sample. These calculations produce the maximum possible orotate and orotidine values for these control subject collection periods. When orotate or orotidine were not detectable in study patients the sample is recorded as below detection limits (nd).
**allopurinol not administered to patient #2
Abbreviations: nd, below detection limit; nt, sample not obtained The data in Table 2 demonstrate that the allopurinol test for this unstratified group of tumors has a sensitivity of 0.73 and a specificity of 1.0, when the threshold for a positive test for cancer is set at an orotate and/or orotidine excretion 4

OPRT, orotate phosphoribosylpyrophosphate transferase
OMP, orotidine monophosphate
XO, xanthine oxidase
UK, uridine kinase

I claim:

1. A method of screening for the presence or absence of cancer characterized by increased DNA synthesis in a patient, the method comprising administering to the patient an orotidine monophosphate decarboxylase inhibitor precursor;

thereafter collecting a body fluid sample from the patient; and determining the orotate or orotidine content in the sample relative to a standard or control to correlate the content with the presence or absence of cancer in the patient.

2. The method of claim 1, wherein the body fluid sample is a urine sample.

3. The method of claim 1, wherein the orotidine monophosphate decarboxylase inhibitor precursor is selected from the group consisting of 6-hydroxyuridine, 6-azauridine, uridine, allopurinol and oxipurinol.

4. The method of claim 1, wherein the orotidine monophosphate decarboxylase inhibitor precursor is 6-hydroxyuridine.

5. The method of claim 1, wherein the orotidine monophosphate decarboxylase inhibitor precursor is allopurinol.

6. The method of claim 1, wherein the orotidine monophosphate decarboxylase inhibitor precursor is administered at a dose of about 0.1 to 15 mg/kg per day.

7. The method of claim 1, wherein the orotidine monophosphate decarboxylase inhibitor precursor is administered at a dose of about 0.5 to 10 mg/kg per day.

8. The method of claim 1, wherein said collecting step occurs about 1–30 hours after said administering step.

9. The method of claim 1, further comprising, before said determining step, repeating said collecting step at least once and averaging the content of orotate or orotidine in each collecting step to produce an average content of orotate or orotidine in the sample, wherein the average content is thereafter used in said determining step.

10. The method of claim 9, wherein the repeated collecting steps occur sequentially about every 2–10 hours after the first collecting step.

11. A method of monitoring the effectiveness of treatment of cancer characterized by increased DNA synthesis in a patient, the method comprising (a) administering to the patient an orotidine monophosphate decarboxylase inhibitor precursor;

(b) thereafter collecting a body fluid sample from the patient;

(c) determining a first orotate or orotidine content in the sample;

(d) thereafter treating the cancer with a cancer treatment;

(e) repeating steps (a)–(c) to determine a second orotate or orotidine content in the sample; and (f) comparing the first content with the second content to monitor the effectiveness of the cancer treatment.

* * * * *